United States Patent [19]

Hsu et al.

[11] Patent Number: 4,485,245
[45] Date of Patent: Nov. 27, 1984

[54] HYDROGENATION OF CARBOXYLIC ACID ANHYDRIDES TO LACTONES OR ESTERS USING A RUTHENIUM TRICHLOROSTANNATE CATALYST

[75] Inventors: Chao-Yang Hsu, Media; James E. Lyons, Wallingford, both of Pa.

[73] Assignee: Sun Tech, Inc., Philadelphia, Pa.

[21] Appl. No.: 437,724

[22] Filed: Oct. 29, 1982

[51] Int. Cl.³ .................. C07D 307/20; C07D 307/83
[52] U.S. Cl. .................... 549/302; 549/325; 549/311; 549/307; 560/1; 560/122; 560/106; 560/265
[58] Field of Search ............... 549/325, 302, 307, 311; 560/265, 106, 1, 122

[56] References Cited

U.S. PATENT DOCUMENTS 3,957,827 5/1976 Lyons ................................. 549/325
3,968,133 7/1976 Knifton ............................... 560/233

*Primary Examiner*—Jane T. Fan
*Attorney, Agent, or Firm*—J. Edward Hess; Donald R. Johnson; Standford M. Back

[57] ABSTRACT

Process for selective homogeneous catalytic hydrogenation of carboxylic acid anhydrides to ester or lactones at an improved rate and to obtain improved yields wherein the catalyst is a ruthenium trichlorostannate complex of the formula:

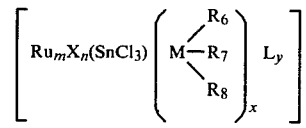

wherein X is hydrogen, chlorine, bromine, iodine or lower alkyl; m is the integer 1 or 2; n is an integer of from 0 to 3 but when n is 2 or 3, X may be the same or different; M is P, As or Sb; $R^6$, $R^7$ and $R^8$ independently are lower alkyl, cycloalkyl, aryl, benzyl or a bidentate legand; x is an integer of from 1 to 4 but when x is 2 or more, M may be the same or different; L is a neutral ligand, olefin, CO or $(R^9)_2CO$ wherein $R^9$ is lower alkyl; y is an integer of from 0 to 3 but when y is 2 or 3, L may be the same or different; and the sum of x and y is at least 2.

9 Claims, No Drawings

HYDROGENATION OF CARBOXYLIC ACID ANHYDRIDES TO LACTONES OR ESTERS USING A RUTHENIUM TRICHLOROSTANNATE CATALYST

BACKGROUND OF THE INVENTION

This invention relates to an improved catalytic process for the hydrogenation of acyclic and cyclic carboxylic acid anhydrides to esters and lactones, respectively. More particularly, this invention relates to the foregoing process wherein the reaction takes place under mild conditions in the presence of an organometallic ruthenium trichlorostannate complex catalyst in homogeneous solution.

U.S. Pat. No. 3,957,827 to J. E. Lyons, issued May 18, 1976, describes the selective catalytic hydrogenation of acyclic and cyclic carboxylic acid anhydrides to esters and lactones wherein the catalyst is a ruthenium complex of the formula (I):

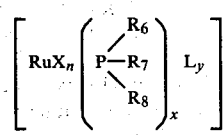

where X is hydrogen, chlorine, bromine, iodine or lower alkyl; n is an integer of from 0 to 2, but when n is 2, X may be the same or different; L is a neutral ligand, olefin or CO; y is an integer of from 0 to 3, but when y is 2 or 3, L may be the same or different; $R_6$, $R_7$ and $R_8$ are lower alkyl, cycloalkyl of from 5 to 15 carbon atoms, aryl, benzyl or a bidentate ligand, and each of the R groups may be the same or different; and x is an integer of from 1 to 3. The reaction occurs readily under mild reaction conditions in homogeneous solution and is characterized by good selectivity and yield, and does not proceed beyond ester or lactone formation.

SUMMARY OF THE INVENTION

According to the present invention the rate of the hydrogenation process of U.S. Pat. No. 3,957,827 is substantially improved, in some cases of the order of four-to five-fold, by employing as the catalyst a ruthenium trichlorostannate complex of the formula (II):

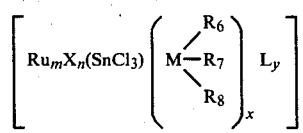

wherein X is as specified in formula I above, m is 1 or 2; n is an integer of from 0 to 3 but when n is 2 or 3, X may be the same or different; M is P (phosphorus), As (arsenic) or Sb (antimony); $R^6$, $R^7$ and $R^8$ independently are lower alkyl (for example, from 1 to 8 carbon atoms), cycloalkyl (for example, from 5 to 15 carbon atoms), aryl, benzyl or a bidentate ligand; x is an integer of from 1 to 4 but when X is 2 or more, M can be the same or different; L is a neutral ligand, olefin, CO or $(R^9)_2CO$ wherein $R^9$ is lower alkyl; y is an integer of from 0 to 3 but when y is 2 or 3, L may be the same or different; and the sum of x and y is at least 2.

DETAILED DESCRIPTION

In respects other than use of ruthenium catalyst of formula II above, the hydrogenation conditions of the present invention are essentially the same as described in U.S. Pat. No. 3,957,827: the reaction proceeds under mild conditions of temperature and pressure, e.g., about 50°–150° C., preferably 90°–110° C., and about 40–400 psi hydrogen, preferably 100–150 psi. The higher hydrogen pressures favor a faster rate of hydrogenation. Conventional solvents for homogeneous catalytic reactions are employed, such as benzene or toluene.

The hydrogenation reaction using a catalyst of formula II proceeds as in U.S. Pat. No. 3,957,827 and is summarized below in equations 1 and 2.

Acyclic acid anhydride to ester

wherein R and $R^1$ independently are lower alkyl (for example, from 1 to 8 carbon atoms), cycloalkyl (for example, from 5 to 15 carbon atoms) or aryl.

Cyclic acid anhydride to lactone:

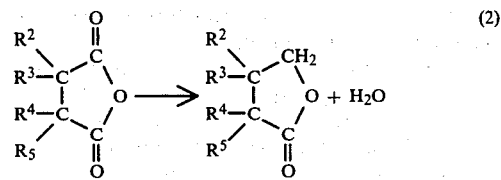

wherein $R^2$, $R^3$, $R^4$ and $R^5$ independently are hydrogen, lower alkyl, cycloakyl or aryl; and wherein the R groups taken together may form a saturated or unsaturated ring having, for example, from 5 to 8 carbon atoms, or an aromatic ring, both monocyclic and condensed.

As in U.S. Pat. No. 3,957,827 the acyclic carboxylic acid anhydrides precursors (equation 1 above) are exemplified by acetic anhydride, propionic anhydride, benzoic acid anhydride and mixed anhydrides of similar structure. Upon hydrogenation in accordance with the present invention the ester products obtained include ethyl acetate, butyl propionate, benzyl benzoate, and the like. The cyclic anhydride starting materials (equation 2 above) include succinic anhydride, glutaric anhydride and the like. Typical lactone products of equation 2 include gamma-lactone, phthalide and the gamma-lactone from naphthalene-1, 2-dicarboxylic acid anhydride.

Among the ruthenium trichlorostannate complexes of formula II useful in the process of this invention may be mentioned the following:
[RuCl(SnCl$_3$)(PPh$_3$)$_2$]
[Ru$_2$Cl$_3$(SnCl$_3$)(CO)$_2$(PPh$_3$)$_4$]
[Ru$_2$Cl$_3$(SnCl$_3$)(CO)$_2$(PPh$_3$)$_2$(Me$_2$CO)$_2$]
[RuH(SnCl$_3$)(PPh$_3$)$_3$]
[RuCl(SnCl$_3$)(P tolyl$_3$)$_3$]
[RuCl(SnCl$_3$)(P cyclohexyl$_3$)$_3$]
[RuCl(SnCl$_3$)(DIPHOS)]
[RuCl(SnCl$_3$)(ARPHOS)]
wherein Ph is phenyl, Me is methyl, DIPHOS is (PPh$_3$)$_2$ and ARPHOS is AsPh$_3$PPh$_3$. Preferably, in formula II, when m is 1, n is also 1 and x+y is 3. When m is 2, n preferably is 3 and x+y is from 5 to 8. Typical L groups are CO, $(CH_3)_2CO$, ketone, lactone, ether, $(R^{10})_3As$ and $(R^{10})_3N$ where $R^{10}$ is a hydrocarbon group such as lower alkyl (e.g., $C_1-C_8$) or cyclic alkyl (e.g., $C_5-C_{15}$). The L groups may be the same or different.

While the catalysts of formula II include those complexes resulting from substitution of $SnCl_3$ for one of the X groups in the complexes of formula I, it will be evident that a variety of other compounds are additionally included within the scope of formula II. Moreover, anionic and salt forms of the complexes are suitable, depending on the extent to which such electrolytes are compatible with other components of the homogeous reaction medium.

The complexes of formula II are prepared as described by Stephenson and Wilkinson, J. Inorg. Nucl. Chem. 28 (1966) 945-956 and by Antonov et al, Khim. Khim. Tekhnol., 1981, 24 (6), 663-665 (abstracted in Platinum Metals Review, 26(1), January 1982, page 44). The catalysts may also be generated in situ during or prior to the hydrogenation process by introducing $SnCl_2$ as a powder or solvent solution, preferably in molar excess, into a reaction mixture of the starting anhydride, precursor complex of formula I (or other precursor such as described in the above article by Stephenson and Wilkinson) and solvent medium. Alternatively, the $SnCl_2$ may be added before or during introduction of the anhydride.

During the hydrogenation reaction of U.S. Pat. No. 3,957,827 the catalyst (formula I above), when in halide form or when otherwise containing releasable halide such as chloride, reacts with a portion of the hydrogen to form HCl and a ruthenium hydride, typically as follows (equation 3):

The liberated HCl then catalyzes the hydrolysis of starting anhydride to substantial proportions (50% in some cases) of the corresponding acid. The acid may then be recovered, dehydrated, and recycled to the reactor.

A similar reaction can take place with catalysts of the present invention (equation 4) when, for example, X is halogen and n is 1 or more:

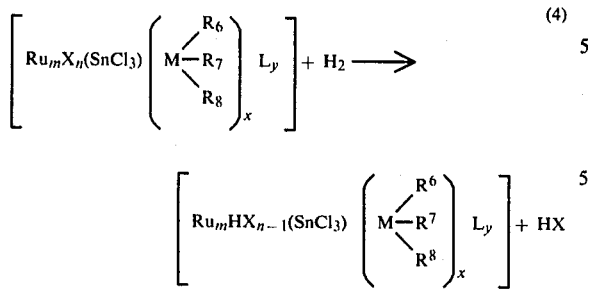

To avoid, minimize or offset such hydrolysis, U.S. Pat. No. 3,957,827 recommends the use of water scavengers such as molecular sieves, a dehydrating agent such as $MgSO_4$ or the like. Dehydration and recycling of the hydrolyzed material are also thereby avoided. However, the catalyst of the present invention (formula II), being a more active hydrogenation catalyst, will cause the hydrogenation reaction to be favored over the hydrolysis reaction. Consequently, less attention to water scavenging and recycling of hydrolyzed product is required when using the catalysts of the present invention, and higher yields of ester or lactone can be expected. Nevertheless, dehydration can also be practiced as in U.S. Pat. No. 3,957,827, including the use of organic dehydrating agents such as ketals and acetals (e.g., 2,2-dimethoxypropane, methylal, 1,1-dimethoxycyclohexane, and the like) and orthoformates (e.g., methylorthoformate, ethylorthoformate, and the like).

The catalyst may be recovered in any convenient manner, for example by precipitation after crystallization of the ester or lactone product. Alternatively, the products may be separated from the reaction mixture and the remaining catalyst solution may be reused without precipitation of the catalyst, with addition of fresh catalyst as needed.

The following examples further describe the invention.

EXAMPLE 1

Succinic anhydride, 20.0 g., toluene, 40 ml., $[RuCl_2(PPh_3)_3]$, 1.0 g., and stannous chloride, 1.5 g., are stirred in a suitable reaction vessel at 125° C. under a hydrogen pressure of 200 psig. The reaction is run until hydrogen adsorption has stopped, after which time the mixture is stirred an additional 2 hours (at reaction temperature and under reaction pressure). The reaction mixture is filtered while hot under an inert atmosphere of nitrogen and the solution allowed to cool. The product, gamma-butyrolactone, is recovered and purified by re-crystallization from toluene. A good yield is obtained.

EXAMPLE 2

The reaction of Example 1 is repeated in all essential respects except that phthalic anhydride is used in place of succinic anhydride. A good yield of phthalide is obtained.

EXAMPLE 3

The reaction of Example 1 is repeated in all essential respects except that acetic anhydride is used in place of succinic anhydride. Ethyl acetate is obtained in good yield.

EXAMPLE 4

The reactions of Examples 1-3 are repeated in all essential respects except that the reactions are run at 75° C. and 50 psi hydrogen pressure, and the amount of stannous chloride added to the reaction mixture is 3.0 g. Good yields of the lactones or esters are obtained.

EXAMPLE 5

The reactions of Examples 1-3 are repeated in all essential respects except that the following catalysts, prepared prior to addition to the reaction mixture, are used:

$[RuCl(SnCl_3)(PPh_3)_2]$
$[Ru_2Cl_3(SnCl_3)(CO)_2(PPh_3)_4]$
$[Ru_2Cl_3(SnCl_3)(CO)_2(PPh_3)_2(Me_2CO)_2]$
$[RuH(SnCl_3)(PPh_3)_3]$

The reactions proceed rapidly and good yields of the lactones or esters are obtained.

We claim

1. In a process for the selective hydrogenation of acyclic and cyclic carboxylic acid anhydrides to form esters or lactones which comprises reacting hydrogen, at elevated temperature and pressure, with the acyclic or cyclic carboxylic anhydride in homogeneous solution in the presence of a ruthenium catalyst, wherein the anhydride is selected from

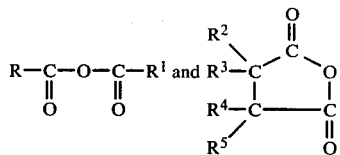

to form

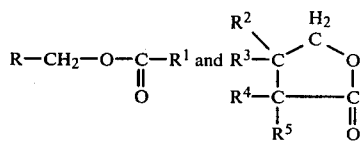

respectively, wherein R and $R^1$ independently are lower alkyl, cycloalkyl ($C_5$-$C_{15}$), or aryl, and $R^2$, $R^3$, $R^4$ and $R^5$ independently are hydrogen, lower alkyl, cycloalkyl ($C_5$-$C_{15}$), or aryl, and $R^3$ and $R^4$ when taken together may form a saturated ring, or aromatic ring, the improvement wherein the catalyst is a ruthenium trichlorostannate of the formula

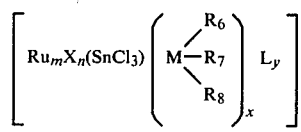

wherein X is hydrogen, chlorine, bromine, iodine or lower alkyl; m is the integer 1 or 2; n is an integer of from 0 to 3 but when n is 2 or 3, X may be the same or different; M is P, As or Sb; $R^6$, $R^7$ and $R^8$ independently are lower alkyl, cycloalkyl($C_5$-$C_{15}$), aryl, benzyl or a bidentate legand; x is an integer of from 1 to 4 but when x is 2 or more, M may be the same or different; L is a neutral ligand, olefin, CO, or $(R^9)_2CO$ wherein $R^9$ is lower alkyl; y is an integer of from 0 to 3 but when y is 2 or 3, L may be the same or different; and the sum of x and y is at least 2.

2. The process of claim 1 wherein the anhydride is phthalic anhydride and the lactone is phthalide.

3. The process of claim 1 wherein the anhydride is succinic anhydride and the product is gamma butyrolactone.

4. The process of claim 1 wherein the anhydride is acetic anhydride and the product is ethyl acetate.

5. the process of claim 1 wherein the catalyst is [RuCl(SnCl$_3$)(PPh$_3$)$_2$].

6. The process of claim 1 wherein the catalyst is [Ru$_2$Cl$_3$(SnCl$_3$)(PPh$_3$)$_4$(CO)$_2$].

7. The process of claim 1 wherein the catalyst is [Ru$_2$Cl$_3$(SnCl$_3$)(PPh$_3$)$_3$(CO)$_2$(CH$_3$)$_2$CO].

8. The process of claim 1 wherein the temperature is about 50° C. to 150° C. and the hydrogen is about 40 to 400 psi.

9. The process of claim 1 wherein the catalyst is generated in situ by addition of stannous chloride to a reaction mixture containing the anhydride and the precursor of the catalyst.

* * * * *